US010309962B2

(12) United States Patent
Jones et al.

(10) Patent No.: US 10,309,962 B2
(45) Date of Patent: Jun. 4, 2019

(54) DIAGNOSTIC REAGENTS

(71) Applicant: THE SECRETARY OF STATE FOR ENVIRONMENT, FOOD AND RURAL AFFAIRS, Surrey (GB)

(72) Inventors: Gareth Jones, Surrey (GB); Hans Vordermeier, Surrey (GB)

(73) Assignee: The Secretary of the State for Environment, Food & Rural Affairs acting through the Animal and Veterinary Laboratories Agency (GB)

(*) Notice: Subject to any disclaimer, the term of this patent is extended or adjusted under 35 U.S.C. 154(b) by 45 days.

(21) Appl. No.: 15/343,522

(22) Filed: Nov. 4, 2016

(65) Prior Publication Data

US 2017/0097349 A1 Apr. 6, 2017

Related U.S. Application Data

(60) Continuation of application No. 14/493,950, filed on Sep. 23, 2014, now abandoned, which is a division of application No. 13/810,945, filed as application No. PCT/GB2011/051343 on Jul. 18, 2011, now abandoned.

(30) Foreign Application Priority Data

Jul. 19, 2010 (GB) .................................. 1012072.3

(51) Int. Cl.

| | |
|---|---|
| ***A61K 49/00*** | (2006.01) |
| ***C07K 7/08*** | (2006.01) |
| ***G01N 33/569*** | (2006.01) |
| ***C07K 14/35*** | (2006.01) |

(52) U.S. Cl.

CPC ..... *G01N 33/5695* (2013.01); *A61K 49/0006* (2013.01); *C07K 7/08* (2013.01); *C07K 14/35* (2013.01); *G01N 2333/35* (2013.01); *G01N 2333/7156* (2013.01)

(58) Field of Classification Search

None

See application file for complete search history.

(56) References Cited

U.S. PATENT DOCUMENTS

| | | | |
|---|---|---|---|
| 6,613,881 | B1 | 9/2003 | Alderson et al. |
| 2015/0093766 | A1 | 4/2015 | Jones et al. |

FOREIGN PATENT DOCUMENTS

| | | | |
|---|---|---|---|
| WO | 98/53075 A2 | 11/1998 | |
| WO | 98/53076 A2 | 11/1998 | |
| WO | 01/04151 A2 | 1/2001 | |
| WO | 01/62893 A2 | 8/2001 | |
| WO | 2009/060184 A1 | 5/2009 | |
| WO | 2011/135369 A1 | 11/2011 | |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000, 10:398-400).*
Greenspan et al. (Nature Biotechnology 7: 936-937, 1999).*
Accession No. AYB28121, "Mycobacterium tuberculosis ESAT-6 like protein fragment Rv2346c/Rv1793". (Jul. 8, 2010).
Aggerbeck et al., "Safety of ESAT-6", Tuberculosis, 2006, pp. 363-373, vol. 86.
Arend et al., "Detection of Active Tuberculosis Infection by T Cell Responses to Early-Secreted Antigenic Target 6-kDa Protein and Culture Filtrate Protein 10", The Journal of Infectious Diseases, 2000, pp. 1850-1854, vol. 181.
Berg et al., "The Burden of Mycobacterial Disease in Ethiopian Cattle: Implications for Public Health", PLoS One, 2009, e5068, 8 pgs., vol. 4, No. 4.
Berggren, "Field Experiment With BCG Vaccine in Malawi", British Veterinary Journal, 1981, pp. 88-94, vol. 137.
Bork, "Powers and Pitfalls in Sequence Analysis: The 70% Hurdle", Genome Research, 2000, pp. 398-400, vol. 10.
Bowie et al., "Deciphering the Message in Protein Sequences: Tolerance to Amino Acid Substitutions", Science, 1990, pp. 1306-1310, vol. 247, No. 4948.
Buddle et al., "Differentiation between *Mycobacterium bovis* BCG-Vaccinated and *M. bovis*-Infected Cattle by Using Recombinant Mycobacterial Antigens", Clinical and Diagnostic Laboratory Immunology, 1999, pp. 1-5, vol. 6, No. 1.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, 1990, pp. 2129-2138, vol. 111.
Corbett et al., "The Growing Burden of Tuberculosis: Global Trends and Interactions With the HIV Epidemic", Arch. Intern Med, 2003, pp. 1009-1021, vol. 163.
Database Accession No. Q6MX18, *sequence*, Anonymous: "ESAT-6 Like Protein ESXS", XP-002764442, Oct. 31, 2006, retrieved from NCBI, 1 pg.
Database Accession No. ZP_05765522.1, *sequence*, Anonymous: "hypothetical protein MtubCP_18788 [*Mycobacterium tuberculosis* CPHL_A]", XP-002764443, Oct. 1, 2009, retrieved from NCBI, 1 pg.
Dean et al., "Minimum Infective Dose of *Mycobacterium bovis* in Cattle", Infection and Immunity, 2005, pp. 6467-6471, vol. 73, No. 10.
European Search Report from European Application No. 16188822.7, dated Dec. 6, 2016, 11 pgs.

(Continued)

*Primary Examiner* — Robert A Zeman

(57) ABSTRACT

There is provided a diagnostic reagent useful to determine whether an animal has a tuberculosis infection or has been exposed to a tuberculosis agent, for example a *Mycobacterium*. The reagent is useful to distinguish between such an animal and an animal which has been vaccinated against a tuberculosis infection.

10 Claims, 5 Drawing Sheets

Specification includes a Sequence Listing.

(56) References Cited

OTHER PUBLICATIONS

Hogarth et al., "Development of vaccines against bovine tuberculosis", Journal of Pharmacy and Pharmacology, 2006, pp. 749-757, vol. 58.

Jones et al., "Screening of Predicted Secreted Antigens from *Mycobacterium bovis* Reveals the Immunodominance of the ESAT-6 Protein Family", Infection and Immunity, 2010, pp. 1326-1332, vol. 78, No. 3.

Jones et al., "Screening of Predicted Secreted Antigens from *Mycobacterium bovis* Identifies Potential Novel Differential Diagnostic Reagents", Clinical and Vaccine Immunology, 2010, pp. 1344-1348, vol. 17, No. 9.

Krebs et al., "Bovine Tuberculosis in Cattle and Badgers", Report by the Independent Scientific Review Group, 1997, HMSO, London, United Kingdom, 196 pgs.

Lazar et al., "Transforming Growth Factor α: Mutation of Aspartic Acid 47 and Leucine 48 Results in Different Biological Activities", Molecular and Cellular Biology, 1988, pp. 1247-1252, vol. 8, No. 3.

Millington et al., "Rv3615c is a highly immunodominant RD1 (Region of Difference 1)-dependent secreted antigen specific for *Mycobacterium tuberculosis* infection", PNAS, 2011, pp. 5730-5735, vol. 108, No. 14.

Monaghan et al., "The tuberculin test", Veterinary Microbiology, 1994, pp. 111-124, vol. 40.

Plum, "A Study of Avian Tuberculosis in Cattle", Cornell Vet., 1931, pp. 68-76, vol. 21.

Sidders et al., "Screening of Highly Expressed Mycobacterial Genes Identifies Rv3615c as a Useful Differential Diagnostic Antigen for the *Mycobacterium tuberculosis* Complex", Infection and Immunity, 2008, pp. 3932-3939, vol. 76, No. 9.

Stenius, "Differentiation by Tuberculin Testing of Infection in Cattle due to the Human, Bovine and Avian Types of Tubercle Bacilli", The Veterinary Record, 1938, pp. 633-637, vol. 50, No. 22.

Tjernberg et al., "DMSO-Related Effects in Protein Characterization", Journal of Biomolecular Screening, 2006, pp. 131-137, vol. 11, No. 2.

Vordermeier et al., "Development of Diagnostic Reagents to Differentiate between *Mycobacterium bovis* BCG Vaccination and *M. bovis* Infection in Cattle", Clinical and Diagnostic Laboratory Immunology, 1999, pp. 675-682, vol. 6, No. 5.

Vordermeier et al., "Use of Synthetic Peptides Derived from the Antigens ESAT-6 and CFP-10 for Differential Diagnosis of Bovine Tuberculosis in Cattle", Clinical and Diagnostic Laboratory Immunology, 2001, pp. 571-578, vol. 8, No. 3.

Waddington et al., "An Experiment to Challenge the Resistance to Tuberculosis in B.C.G. Vaccinated Cattle in Malawi", British Veterinary Journal, 1972, pp. 541-552, vol. 128.

Whelan et al., "Development of a Skin Test for Bovine Tuberculosis for Differentiating Infected from Vaccinated Animals", Journal of Clinical Microbiology, 2010, pp. 3176-3181, vol. 48, No. 9.

Wu et al., "Recombinant early secreted antigen target 6 protein as a skin test antigen for the specific detection of *Mycobacterium tuberculosis* infection", Clinical and Experimental Immunology, 2008, pp. 81-87, vol. 152.

Lightbody et al., "Characterisation of complex formation between members of the *Mycobacterium tuberculosis* complex CFP-10/ESAT-6 protein family: towards an understanding of the rules governing complex formation and thereby functional flexibility," FEMS Microbiology Letters, 2004, pp. 255-262, vol. 238.

* cited by examiner

DIAGNOSTIC REAGENTS

CROSS-REFERENCE TO RELATED APPLICATION

This patent application is a continuation of U.S. patent application Ser. No. 14/493,950, filed Sep. 23, 2014, which is a divisional of U.S. patent application Ser. No. 13/810,945, filed Mar. 22, 2013, which is a National Stage of International Patent Application No. PCT/GB2011/051343, filed Jul. 18, 2011, which claims benefit of GB 1012072.3, filed Jul. 19, 2010, the disclosure of each is hereby incorporated by reference in its entirety.

FIELD OF THE INVENTION

The present invention relates to reagents for use in the detection of tuberculosis infections, particularly tuberculosis in mammals such as human beings and cattle, more particularly infection by Mycobacteria such as *M. tuberculosis* and *M. bovis*. The reagents are useful to differentiate between animals with a tuberculosis infection and those which have been vaccinated against infection, as a positive result is only obtained from infected animals (or animals exposed to an infectious agent).

BACKGROUND

*M. tuberculosis* and *M. bovis* are important pathogens of man and animals. *M. tuberculosis* is thought to infect up to a third of the world's human population, remaining undetected during a latent phase of infection and reactivating to cause 10 million cases of tuberculosis and other diseases per year, resulting in 2 million deaths (Corbett et al. (2003) Arch. Intern. Med. vol. 163 pp 1009-1021). *M. bovis*, which has more than 99.9% sequence identity with *M. tuberculosis*, is the predominant causative agent of bovine tuberculosis (BTB) and also causes disease in human. Cases of bovine tuberculosis in cattle caused by *M. tuberculosis* have also been reported, particularly in developing countries with high incidence rates of human TB (see, for example, Berg et al.(2009) PLoS ONE vol. 4 e5068). BTB represents a significant economic burden to the agricultural industries of various countries including the United Kingdom (Krebs (1997) "Bovine Tuberculosis in Cattle & Badgers" HMSO, London, United Kingdom).

The primary diagnostic test used in the control and surveillance of bovine TB is the tuberculin skin-test, a test that has remained in the forefront of TB diagnosis in both man and cattle for over 100 years. The development of the test arose following the preparation of the first 'tuberculin' by Robert Koch in 1890. Whilst Koch's tuberculin failed to live up to its initial claims of having curative properties, its diagnostic potential was quickly realised. The most common formats of the test used in cattle are the caudal fold test (CFT), the single intradermal cervical tuberculin test (SIT) and the single intradermal comparative cervical tuberculin test (SICCT) (Monaghan et al. (1994) Vet. Microbiol. vol. 40 pp 111-24). Both test formats use a purified protein derivative (PPD) tuberculin prepared from a culture of *M. bovis* (PPD-B) as the primary diagnostic antigen. Additionally, the SICCT test includes the use of a *M. avium* derived PPD (PPD-A) to provide a measure of environmental sensitisation. It is the more specific of the two tests (Plum (1931) Cornell Vet. vol. 21 pp 68-76; Stenius (1938) Veterinary Record vol. 50 pp 633-7) and is therefore the adopted test format in the UK.

In addition to skin tests, blood-based diagnostic assays that measure antigen-induced lymphokine production such as the interferon gamma (IFN-γ) are also under consideration. The cytokine IFN-γ appears to be critical in the development of immunity to *M. tuberculosis*. For example, both mice with a disrupted IFN-γ gene and humans with mutated IFN-γ receptor are highly susceptible to mycobacterial infections. However, specificity constraints are associated with the use of PPD in such assays. These arise due to the crude mixture of *M. bovis* proteins that PPD contains, many of which are cross-reactive with the BCG vaccine strain and environmental mycobacterial species such as *M. avium* and *M. intracellulare.*

The term "tuberculosis infection assay" used in the present specification may refer to any of these diagnostic tests referred to above.

Bovine TB is a significant and ongoing problem in the UK. Cattle vaccination has been identified as one of the most promising long term UK control strategies (Krebs (1997) "Bovine Tuberculosis in Cattle & Badgers" HMSO) and the development of an efficacious vaccine continues to be a research priority. Currently, promising vaccines against bovine TB are based on heterologous prime-boost combinations that include the live attenuated *M. bovis* vaccine strain Bacille Calmette-Guerin (BCG) as one of their components (Hogarth et al. (2006) J. Pharm. Pharmacol. vol. 58 pp 749-57). However, as in humans, vaccination of cattle with BCG compromises the specificity of the tuberculin skin-test since PPD contains cross reactive antigens shared by both pathogenic and vaccine strains (Berggren (1981) Br. Vet. J. vol. 137 pp 88-94; Buddle et al. (1999) Clin. Diagn. Lab. Immunol. vol. 6 pp 1-5; Waddington & Ellwood (1972) Br. Vet. J. vol. 128 pp 541-52). Therefore, the development of diagnostic tests that can differentiate vaccinated from infected animals, so-called DIVA tests, are an essential pre-requisite to allow the inclusion of BCG-based vaccination as part of bovine TB control strategies.

Previous studies have demonstrated that diagnostic reagents which distinguish between vaccinated and infected cattle can be developed using specific, defined antigens that are present in virulent *M. bovis* but absent from the BCG. Genetic analysis of BCG has revealed that several large genomic regions have been deleted during attenuation and subsequent prolonged propagation in culture. These regions have been characterised and antigens from one of these regions, RD1, have been studied extensively in several species including humans and cattle. For example, it has been demonstrated that protein or peptide cocktails composed of two RD1 region antigens, ESAT-6 and CFP-10, can be used to distinguish between *M. bovis* infected and BCG-vaccinated cattle. In humans, synthetic ESAT-6 and CFP-10 peptides are used in an interferon-γ release assay (QUANTIFERON®-TB Gold Test) for TB diagnosis.

The practical application of such DIVA reagents have so far been largely realised through their use in blood-based interferon-γ (IFN-γ) release assays (IGRAs). For example, WO2009/060184 disclosed several polypeptides including epitopes from Rv3615c which were found to be useful to detect *M. bovis* or *M. tuberculosis* infection, using such an assay. This polypeptide has also been confirmed as useful to detect *M. tuberculosis* infection in humans (Millington et al. (2011) Proc. Natl. Acad. Sci. USA vol. 108 pp 5730-5735). Rv3615c is referred to herein using the *M. tuberculosis* genome annotation (genolist.pasteur.fr/TubercuList/, accessed 14 Jul. 2011). In the *M. bovis* genome, it is annotated as Mb3645c (genolist.pasteur.fr/BoviList/, accessed 14 Jul. 2011).

Given the high level of familiarity and wide-spread application of the tuberculin skin-test by veterinarians and clinicians, a DIVA skin-test format would provide a valuable additional test platform. This might especially be the case where the logistics of access to laboratory-based resources is problematic. It is also notable that in recent years there has also been renewed interest in a skin-test based DIVA test for human TB with several reports demonstrating the skin-test potential of ESAT-6 (Aggerbeck & Madsen (2006) Tuberculosis (Edinb.) vol. 86 pp 363-73; Arend et al. (2000) J. Infect. Dis. vol. 181 pp 1850-4; Wu et al. (2008) Clin. Exp. Immunol. vol. 152 pp 81-7).

The present invention accordingly addresses the problem of providing discriminatory diagnostic reagents for the detection of mycobacterial infections, particularly in a DIVA skin-test format.

SUMMARY OF INVENTION

According to a first aspect of the invention, there is provided a diagnostic reagent comprising a polypeptide comprising amino acid sequence SEQ ID NO:7 or a functional variant thereof. The polypeptide may be a polypeptide which is not full length Rv2346c or Rv1793. It may, for example, comprise between 15-65 amino acids, for example, between 15-60 amino acids, 15-50 amino acids, 15-40 amino acids and may, for example, comprise at least 15, 16, 17, 18, 19, 20, 21, 22, 23, 24, 25, 26, 27, 28, 29 or 30 amino acids. This polypeptide elicits a positive result when used in an assay to determine whether an animal has a tuberculosis infection or has been exposed to a tuberculosis agent. Advantageously, the diagnostic reagent can allow a user to differentiate between an animal having a tuberculosis infection and one which has been vaccinated against such an infection, as is disclosed herein for the first time and as will be explained in further detail below. Therefore, the reagent is characterised in that the reagent elicits a negative diagnostic assay result when a tuberculosis infection assay is carried out on a sample from an animal which has been vaccinated against infection by a tuberculosis agent. A negative result is also obtained when the animal is unvaccinated and uninfected (or unexposed to a tuberculosis agent). The animal may be a mammal, for example a cow, a badger or a human being.

The diagnostic reagent may alternatively or further comprise a polypeptide comprising amino acid sequence SEQ ID NO:8 or a functional variant thereof. The polypeptide may be a polypeptide which is not full length Rv3020c. It may, for example, comprise between 15-65 amino acids, for example, between 15-60 amino acids, 15-50 amino acids, 15-40 amino acids and may, for example, comprise at least 15, 16, 17, 18, 19, 20, 21, 22, 23, 24, 25, 26, 27, 28, 29 or 30 amino acids. This polypeptide also elicits a positive result when used in an assay to determine whether an animal has a tuberculosis infection or has been exposed to a tuberculosis agent. Again, the diagnostic reagent can allow a user to differentiate between an animal having a tuberculosis infection and one which has been vaccinated against such an infection. The reagent is, therefore, characterised in that the reagent elicits a negative diagnostic assay result when a tuberculosis infection assay is carried out on a sample from an animal which has been vaccinated against infection by a tuberculosis agent. A negative result is also obtained when the animal is unvaccinated and uninfected (or unexposed to a tuberculosis agent).

None of the polypeptides Rv2346c, Rv1793 or Rv3020c has previously been identified as useful to differentiate between tuberculosis-infected and vaccinated animals.

Optionally or additionally, the diagnostic reagent may alternatively or further comprise at least one polypeptide each comprising at least one of the amino acid sequences SEQ ID NO:1, 2, 3, 4, 5, 6, 9 or 10 or functional variants thereof.

In one embodiment, the diagnostic reagent may comprise all of amino acid sequences SEQ ID NOs:1-9. This may be in the form of individual polypeptides each having an amino acid sequence selected from SEQ ID NOs:1-9, or may be one or more fusion proteins each comprising two or more of SEQ ID NOs:1-9. These sequences were included in peptide pool Sec#1 described herein and shown in Table 3 below.

The term "tuberculosis infection", as used throughout this specification, indicates an infection in which the causative agent is a *Mycobacterium*, for example, *M. tuberculosis, M. bovis*, and/or *M. africanum*. In some cases, the infection can be the result of exposure to a combination of these bacterial species. Likewise, the term "tuberculosis agent" indicates an organism capable of causing tuberculosic symptoms, typically a *Mycobacterium*, for example *M. tuberculosis, M. bovis*, and/or *M. africanum*.

A vaccine which might be administered to an animal to vaccinate against a tuberculosis infection includes the BCG vaccine.

The diagnostic reagent may alternatively or further comprise a polypeptide comprising at least one of the amino acid sequences SEQ ID NOs:50-69 or a functional variant thereof. These sequences were included in peptide pools #11 and #14 described herein and shown in Table 2 below. For example, the diagnostic reagent may comprise SEQ ID NOs:7 and 50-59 and/or SEQ ID NOs:8 and 60-69.

In some embodiments, the diagnostic reagent may further comprise at least one polypeptide each comprising at least one of the amino acid sequences SEQ ID NOs:11-49 or functional variants thereof. By way of non-limiting example, the diagnostic reagent may comprise the polypeptides having amino acid sequences SEQ ID NOs:11, 18, 22, 30 and 45, or may comprise the polypeptides having amino acid sequences SEQ ID NOs:13, 15, 24, 46; in other words, the diagnostic reagent may comprise any combination of polypeptides which each have an amino acid sequence freely selected from those indicated by SEQ ID NOs: 11-49.

Sequences SEQ ID NOs:11-21 are peptides which are fragments of ESAT-6. Sequences SEQ ID NOs:22-31 are peptides which are fragments of CFP-10. Sequences SEQ ID NOs:32-43 are peptides which are fragments of Rv3615c. These sequences are discussed in co-pending application no. PCT/GB2011/050843. SEQ ID NOs:44, 45 and 46 are full-length ESAT-6, CFP-10, and Rv3615c, respectively. SEQ ID NO:47 is the protein MPB83, SEQ ID NO:48 is a fragment of MPB83 and SEQ ID NO:49 is the protein MPB70.

In one embodiment, the diagnostic reagent may comprise SEQ ID NOs:7, 11-42 and 50-59. Alternatively or additionally, the diagnostic reagent may comprise SEQ ID NOs:8, 11-42 and 60-69.

The diagnostic reagent may comprise individual peptide sequences, or may comprise one or more fusion proteins each comprising at least two amino acid sequences selected from SEQ ID NOs:1-69, preferably comprising at least one of SEQ ID NOs:7 or 8.

The diagnostic reagent may be for use in a method of detecting a tuberculosis infection in a mammal, or of detecting exposure of an animal to a tuberculosis agent. Advantageously, the method is capable of confirming such infection or exposure, as differentiated from vaccination. The method may be a skin test such as a caudal fold test (CFT), single intradermal test (SIT) or single intradermal comparative cervical test (SICCT). A positive result is obtained when the animal is infected with (or has been exposed to) a tuberculosis agent and a negative result is obtained if the animal is not so infected or exposed, even if the animal has been vaccinated against infection by a tuberculosis agent.

In some embodiments, for example for use in a skin test, the diagnostic reagent may be in the form of a sterile injectable preparation which may be an aqueous or an oleaginous suspension, or a suspension in a non-toxic parenterally-acceptable diluent or solvent. The aqueous suspension may be prepared in, for example, mannitol, water, Ringer's solution or isotonic sodium chloride solution. Alternatively, it may be prepared in phosphate buffered saline solution. The oleaginous suspension may be prepared in a synthetic monoglyceride, a synthetic diglyceride, a fatty acid or a natural pharmaceutically-acceptable oil. The fatty acid may be an oleic acid or an oleic acid glyceride derivative. The natural pharmaceutically-acceptable oil may be an olive oil, a castor oil, or a polyoxyethylated olive oil or castor oil. The oleaginous suspension may contain a long-chain alcohol diluent or dispersant, for example, Ph. Hely.

Therefore, according to a second aspect of the invention, there is provided a method of detecting a tuberculosis infection in an animal, or exposure of an animal to a tuberculosis agent, comprising the steps of (i) contacting a population of cells from the animal with at least one diagnostic reagent as defined in the first aspect of the invention; and (ii) determining whether the cells of said population recognise the diagnostic reagent.

Such a method is a "tuberculosis infection assay", as referred to above and described herein. The population of cells may include T-cells. Recognition of the diagnostic reagent by said cells may be by way of, for example, binding of a T cell receptor to the diagnostic reagent, for example, binding of the T cell receptor to at least one polypeptide included in the diagnostic reagent. The method may comprise a cell-mediated immunity (CMI) assay, which may detect interferon gamma (IFN-γ) as described herein.

According to a related aspect of the invention, there is provided a method of detecting a tuberculosis infection in an animal, or exposure of an animal to a tuberculosis agent, comprising conducting a skin test on the animal using at least one diagnostic reagent according to the first aspect of the invention. This is also considered to be a "tuberculosis infection assay" as referred to above. "Using" and "use" of polypeptides and diagnostic reagents in the skin test included in the method typically involves intradermal injection of the polypeptide(s) and/or diagnostic reagent into the animal. The skin test may be a CFT, SIT or SICCT test, as described in the Office International des Epizooties (OIE) Manual of Diagnostic Tests and Vaccines for Terrestrial Animals (ISBN-10:92-9044-718-4; or oie.int/eng/normes/mmanual/a_summry.htm, accessed 14 Jul. 2011). The manual provides information, definitions and guidelines on positive test criteria.

The methods according to this aspect of the invention may be for detecting *M. bovis* or *M. tuberculosis* infection in an animal, for example (but not limited to) a mammal such as a cow, badger or human being. Advantageously, because the diagnostic reagents are able to differentiate between an infected animal and a vaccinated animal, the user can be sure that a positive result from the method is a true positive indicating infection, rather than a false positive resulting from earlier vaccination of the animal. Therefore, the methods in this aspect of the invention provide a method of detecting a tuberculosis infection in an animal, or exposure of an animal to a tuberculosis agent, comprising conducting a skin test on the animal using at least one diagnostic reagent according to the first aspect of the invention, wherein use of the method on an animal which has been vaccinated against infection by a tuberculosis agent results in a negative skin test being obtained and use of the method on an animal infected with a tuberculosis agent results in a positive skin test being obtained.

According to a third aspect of the invention, there is provided a diagnostic kit comprising a diagnostic reagent according to the first aspect of the invention. The diagnostic kit may be for use in one or more methods according to the second aspect of the invention. Particularly where the kit is for use in a skin test method, the diagnostic reagent may be in liquid form, as outlined above, or may be in solid (for example, lyophilised) form. It may be included in the kit in the form of at least one aliquot of 0.05-0.15 ml containing 1-15 μg of each polypeptide contained in the diagnostic reagent. For example, the kit may comprise aliquots of about 0.05 ml, about 0.06 ml, about 0.07 ml, about 0.08 ml, about 0.09 ml, about 0.1 ml, about 0.11 ml, about 0.12 ml, about 0.13 ml, about 0.14 ml or about 0.15 ml, containing 1-15 μg, 3-12 μg, 5-10 μg of each protein, for example, about 5 μg, about 6 μg, about 7 μg, about 8 μg, about 9 μg or about 10 μg of each polypeptide. Each aliquot may be contained in a disposable injection device. The kit may further comprise at least one sample of PPD. The diagnostic reagent is able to detect a tuberculosis infection in an animal, or exposure of an animal to a tuberculosis agent, for example it may be able to detect infection by or exposure to *M. bovis* or *M. tuberculosis*. Particularly when the diagnostic reagent comprises one or more of SEQ ID NOs:1-9 and/or 50-69, it enables a user to differentiate between a tuberculosis infected animal and an animal which has been vaccinated against a tuberculosis infection, by methods such as described herein. As mentioned above, this enables the user to rely on positive test results when using the diagnostic reagent as an indication of tuberculosis infection rather than of vaccination.

According to a fourth aspect of the invention, there is provided a polypeptide (which may be isolated) comprising or consisting of the amino acid sequence of any of SEQ ID NOs:1-10 or 50-69 or a functional variant thereof. The full length antigen polypeptides listed in Table 3 may be excluded (e.g., Rv1038c, Rv1197, Rv1792, etc.). Such a polypeptide may form a component of a diagnostic reagent according to the first aspect of the invention. The term "functional variant" indicates a polypeptide in which the amino acid sequence differs from the base sequence from which it is derived in that one or more amino acids within the sequence are substituted for other amino acids. The variant is a functional variant because the functional characteristics of the polypeptide from which the variant is derived are maintained. For example, a similar immune response is elicited by exposure of an animal, or a sample from an animal, to the variant polypeptide as compared to the non-variant. In particular, any amino acid substitutions, additions or deletions must not alter or significantly alter the tertiary structure of one or more epitopes contained within the polypeptide from which the variant is derived. The skilled person is readily able to determine appropriate functional variants without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
|---|---|
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the peptide's conformation.

As mentioned above, non-conservative substitutions are possible provided that these do not disrupt the tertiary structure of an epitope within the polypeptide, for example, which do not interrupt the immunogenicity (for example, the antigenicity) of the peptide. In particular, the addition or deletion of a small number (for example, up to about 10, or up to about 5, for example about 1, 2, 3, 4 or 5) of amino acids to the N- or C-terminus of a polypeptide may not adversely affect the immunogenicity of the peptide and such variants to an amino acid sequence are particularly envisaged as being included within the term "functional variant" of a polypeptide.

Broadly speaking, fewer non-conservative substitutions will be possible without altering the biological activity of the polypeptide. Suitably, variants may be at least about 50% identical, about 60% identical, for example at least about 75% identical, such as at least about 85%, 90%, 95%, 96%, 97%, 98% or about 99% identical to the base sequence, determined as a percentage of the full length of the longest of the polypeptides being compared.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. The percentage sequence identity may be determined using the BLASTP software, publicly available at blast.ncbi.nlm.nih.gov/Blast.cgi (accessible on 14 Jul. 2011), using default parameter settings. Comparison should be determined for the full length sequence of the polypeptide, to avoid high sequence identity over a short fragment of the polypeptide.

The invention also encompasses fusion proteins comprising more than one of SEQ ID NOs:1-10 and/or 50-69. The full length antigen proteins listed in Table 3 may be excluded (e.g., Rv1038c, Rv1197, Rv1792, etc.).

According to a fifth aspect of the invention, there is provided a nucleic acid encoding a polypeptide comprising at least one of the amino acid sequences SEQ ID NOs:1-10 or 50-69 or a functional variant thereof. The DNA sequence encoding the full-length antigen proteins listed in Table 3 may be excluded (e.g., the Rv1038c gene, the Ry1197 gene, etc.). The nucleic acid may form part of a vector and there is also provided a cell transformed with such a vector.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF FIGURES

Particular non-limiting examples of the present invention will now be described with reference to the following Figures, in which.

Figure 1:
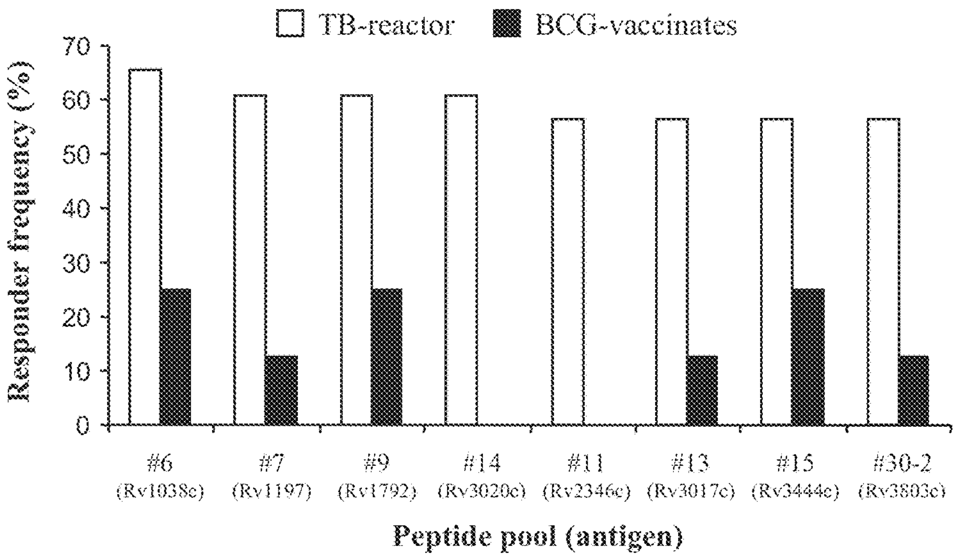
FIG. 1 shows the responder frequency of 23 TB-reactor (TB) and 8 BCG-vaccinated (BCG) animals to the most frequently recognized secretome peptide pools.

#14) (significance between groups determined by repeated measure ANOVA, * $p<0.05$), in cattle naturally exposed to *M. bovis* infection.

EXAMPLES

Materials and Methods

Cattle

All animals were housed at the Veterinary Laboratories Agency at the time of blood sampling and procedures were conducted within the limits of a United Kingdom Home Office Licence under the Animal (Scientific Procedures) Act 1986, which were approved by the local ethical review committee. The following groups of animals were used in this study:

(i) Tuberculosis Reactors (TB-reactors)

Heparinised blood samples were obtained from naturally infected, SICCT positive reactors from herds known to have bovine tuberculosis (BTB) as determined by the Animal Health Agency. Heparinised blood samples were also obtained from 4 animals who were experimentally infected ca. 6 months with an *M. bovis* field strain from Great Britain (AF 2122/97) by intratracheal instillation of $1\times10^3$ CFU as previously described (Dean et al. (2005) Infect. Immun. vol. 73 pp 6467-6471). A detailed post mortem examination of 36 TB-reactor animals revealed visible TB-lesions in all but four animals, confirming the presence of active disease.

(ii) BCG-vaccinated

Heparinised blood samples were obtained from animals vaccinated with BCG as previously described (Vordermeier et al. (1999) Clin. Diagn. Lab. Immunol. vol. 6 pp 675-682). Briefly, calves (ca. 6 months of age) from BTB-free herds were vaccinated with BCG Pasteur by subcutaneous injection of $1\times10^6$ CFU into the side of the neck.

Production and Preparation of Peptides and Antigens 119 proteins secreted, or potentially secreted, from *Mycobacterium bovis* were selected for antigen screening as previously described (Jones et al. (2010) Infect. Immun. vol. 78 pp 1326-1332). Peptides were synthesized (JPT Peptide Technologies GmbH, Berlin, Germany) in pools of 20-mers overlapping by 12 amino acids for each of the genes of interest. In total, 379 peptide pools containing a total of 4129 peptides were evaluated. These peptide pools were dissolved in RPMI 1640 (Gibco, UK) containing 20% dimethyl sulfoxide (DMSO) to obtain a concentration of 1 mg/ml/peptide, and the peptide pools were used to stimulate whole blood at a final concentration of 5m/ml/peptide. Peptides that comprised the pools for some antigens were synthesized individually (Mimotopes Pty Ltd, Clayton, Australia), dissolved in RPMI 1640 containing 20% DMSO to obtain a concentration of 5mg/m1 and used individually to stimulate whole blood at a final concentration of 10 μg/ml, or formulated into additional peptide pools at a concentration of 10μg/ml/peptide. Peptides from ESAT-6 and CFP-10 were formulated to obtain a peptide cocktail as previously described (Vordermeier et al. (2001) Clin. Diagn. Lab. Immunol. vol. 8 pp 571-578) and were used at a final concentration of 5 μg/ml/peptide. This peptide cocktail was used as a 'gold standard' with which to compare the immunogenicities of the other antigens.

Bovine tuberculin (PPD-B) was supplied by the Tuberculin Production Unit at the Veterinary Laboratories Agency, Weybridge, Surrey, UK and was used at a final concentration of 10 μg/ml. Staphylococcal enterotoxin B (SEB; Sigma-Aldritch, UK) was included as a positive control at a final concentration of 1 μg/ml, while whole blood was incubated with RPMI 1640 alone as a negative control.

IFN-γ Enzyme-linked Immunosorbent Assay (ELISA)

Whole blood aliquots (250 μl were added in duplicate to antigen in 96-well plates and incubated at 37° C. in the presence of 5% $CO_2$ for 24 hours, following which plasma supernatants were harvested and stored at −80° C. until required. Quantification of IFN-γ in the plasma supernatants was determined using the Bovigam ELISA kit (Prionics AG, Switzerland). A result was considered positive if the optical density at 450 nm ($OD_{450}$) with antigen minus the $OD_{450}$ without antigen ($\Delta D_{450}$) was ≥0.1 in both of the duplicate wells.

Skin Test Evaluation of Rv2346c (Peptide Pool #11) or Rv3020c (Peptide Pool #14)

Skin-test evaluation of defined protein and peptide antigens was performed in cattle naturally exposed to *M. bovis* infection (n=17). These cattle were recruited as a result of providing positive responses to the single intradermal cervical comparative tuberculin (SICCT) skin-test during routine field surveillance operations.

Antigens were administered at 8 sites per animal (4 on each side of the neck). Antigens were administered in a volume of 100 μl. All defined protein or peptide antigen cocktails were administered at a concentration of 5 ug/ml per cocktail component. The skin thickness was measured at the injection site immediately prior to intradermal administration of antigen. Skin thickness at the injection site was re-measured 72 hours after antigen administration and the increase in skin-thickness over this time is determined. This method is also suitable for determining the reaction in cattle uninfected with *M. bovis*, whether vaccinated or unvaccinated against such infection.

Purified recombinant protein antigens were supplied by Lionex GmbH. The composition of the cocktail of ESAT-6, CFP-10 and Rv3615c was SEQ ID NOs:11-43. A combination of 11 peptides providing a complete sequence overlap for each of the antigens Rv3020c and Rv2346c was used, as listed in Table 2 below (SEQ ID NOs:7 and 50-59 provide complete sequence overlap for Rv2346c and SEQ ID NOs:8 and 60-69 provide complete sequence overlap for Rv3020c). The Rv3020c and Rv2346c cocktails (i.e. peptide pools #14 and #11, respectively, as shown in Table 2) were tested individually and in combination with a cocktail containing the overlapping peptides of ESAT-6, CFP-10 and Rv3615c (i.e., SEQ ID NOs: 11-43), which is itself the subject of co-pending patent application PCT/GB2011/050843.

Results

To test the hypothesis that *M. bovis* secreted proteins are likely to contain immunogenic antigens that can be used to increase the specificity of diagnostic tests, 379 pools of overlapping peptides (4129 peptides in total representing 119 antigens) were screened for their ability to stimulate an IFN-γ response in vitro using whole blood from both TB-reactor (n=23) and BCG-vaccinated animals (n=8). As expected, all TB-reactor and BCG-vaccinated animals responded to PPD-B and to the positive control antigen SEB, whilst 22 TB-reactor animals (96%) and 2 BCG-vaccinated animals (25%) responded to the ESAT-6/CFP-10 peptide cocktail (data not shown). Of the 379 peptide pools, approximately half (n=184) failed to induce IFN-γ in any of the TB-reactor or BCG-vaccinated animals. For the remaining 195 peptide pools, 163 and 77 were recognized by TB-reactor and BCG-vaccinated animals respectively, with 45 being recognised by both groups of animals (Table 1). Encouragingly, with regards to differential diagnostic reagents, 118 different peptide pools were recognized by TB-reactor animals but failed to induce an IFN-γ response in any of the BCG-vaccinated animals studied.

A hierarchy of responses to the different peptide pools was noted, with responder frequencies ranging from 4% to 65% in the TB-reactor animals, and 13% to 38% in the BCG-vaccinated animals (Table 1).

TABLE 1

| Recognition of the secreted antigen peptide pools. | Number of peptide pools recognized (%) | | Number of peptide pools not recognized (%) | |
|---|---|---|---|---|
| | TB-reactors | BCG-vaccinated | TB-reactors | BCG-vaccinated |
| All peptide pools (379 in total) | 163 (43%) | 77 (20%) | 216 (57%) | 302 (80%) |
| TB-reactor pools (163 in total) | 163 (100%) | 45 (28%) | N.A. | 118 (72%) |

FIG. 1 details the responder frequencies for the top 8 most frequently recognised peptide pools, i.e. those that induced an IFN-γ response in more than half of the TB-reactor animals studied. Strikingly, all but one peptide pool (#30-2) represented antigens belonging to the ESAT-6 protein family. Interestingly, peptide pools #11 and #14 were not recognized by any of the BCG-vaccinated animals, suggesting that they contain peptides with potential application as DIVA reagents. The peptides included in these pools are indicated in Table 2.

TABLE 2

| Sequence | SEQ ID NO | Sequence | SEQ ID NO |
|---|---|---|---|
| Peptide Pool #11 (Rv2346c pool) | | Peptide Pool #14 (Rv3020c pool) | |
| MTINYQFGDVDAHGAMIRAQ | 50 | MSLLDAHIPQLIASHTAFAA | 60 |
| DVDAHGAMIRAQAGLLEAEH | 51 | PQLIASHTAFAAKAGLMRHT | 61 |
| IRAQAGLLEAEHQAIVRDVL | 52 | AFAAKAGLMRHTIGQAEQQA | 62 |
| EAEHQAIVRDVLAAGDFWGG | 53 | MRHTIGQAEQQAMSAQAFHQ | 63 |
| RDVLAAGDFWGGAGSVACQE | 7 | EQQAMSAQAFHQGESAAAFQ | 64 |
| FWGGAGSVACQEFITQLGRN | 54 | AFHQGESAAAFQGAHARFVA | 65 |
| ACQEFITQLGRNFQVIYEQA | 55 | AAFQGAHARFVAAAAKVNTL | 66 |
| LGRNFQVIYEQANAHGQKVQ | 56 | RFVAAAAKVNTLLDIAQANL | 67 |
| YEQANAHGQKVQAAGNNMAQ | 57 | VNTLLDIAQANLGEAAGTYV | 68 |
| QKVQAAGNNMAQTDSAVGSS | 58 | QANLGEAAGTYVAADAAAAS | 8 |
| VQAAGNNMAQTDSAVGSSWA | 59 | EAAGTYVAADAAAASSYTGF | 69 |

Figure 2:
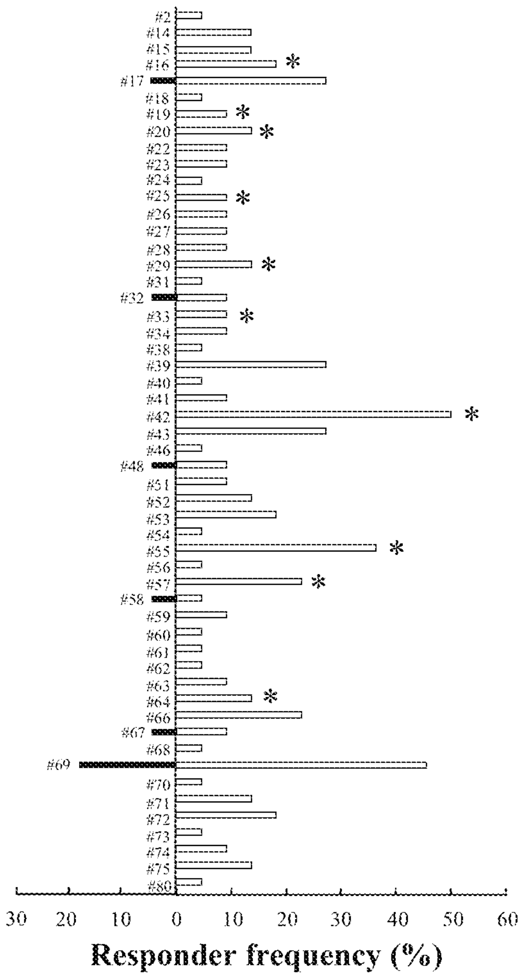
FIG. 2 shows the responder frequencies of 22 TB-reactor animals (open bars) and 23 BCG-vaccinated animals (filled bars) to individual secretome peptides (* indicates peptides selected for inclusion into the Sec#1 peptide pool)

Although 6 out of the top 8 most frequently recognized peptide pools induced IFN-γ responses in some BCG-vaccinated animals, the inventors next reasoned that a fine detail investigation of the immunogenicity of the components of these pools may reveal additional individual peptides with potential use as DIVA reagents. To this end, overlapping peptides contained within these peptide pools were screened individually for their ability to induce IFN-γ production in both TB-reactor (n=22) and BCG-vaccinated (n=23) animals. In these experiments, 19 TB-reactor animals (86%) but no BCG-vaccinated animals (0%) responded to the peptide cocktail (data not shown). Fifty-three individual peptides were identified as immunogenic in TB-reactor animals, with responder frequencies ranging from 5% to 50% (FIG. 2). Of these peptides, six (peptides #17, #32, #48, #58, #67 and #69) also induced IFN-γ responses in BCG-vaccinated animals with responder frequencies ranging from 4% to 17% (FIG. 2).

In order to evaluate whether a combination of individual peptides from different secretome antigens is sufficient to differentially induce an IFN-γ response in TB-reactor animals, a peptide pool (Sec#1) consisting of 10 peptides was constructed. Firstly, peptides #42 and #55 (SEQ ID NOs:7 & 8, respectively) were selected as they were the two most frequently recognised peptides (responder frequencies of 50% and 36% respectively) and also because they belonged to peptide pools not recognised by BCG-vaccinated animals (pools #11 and #14 respectively, FIG. 1). A further four peptides (peptides #20, #29, #33 and #64) were next selected as they were recognised in TB-reactor animals that failed to respond to peptides #42 or #55 (data not shown). Lastly, a further four peptides (peptides #16, #19, #25 and #57) were included due to their location in regions of homology between multiple ESAT-6 proteins (see Table 3).

TABLE 3

Identification of peptides in pools Sec#1 and Sec#2

| Pool | Peptide | SEQ ID | Sequence | Located in antigens: |
|---|---|---|---|---|
| Sec#1 | Pep#16 | 1 | MWASAQNISGAGWSGMAEAT | Rv1038c, Rv1197, Rv1792, Rv2347c, Rv3620c |

TABLE 3-continued

Identification of peptides in pools Sec#1 and Sec#2

| Pool | Peptide | SEQ ID | Sequence | Located in antigens: |
|---|---|---|---|---|
| | Pep#19 | 2 | MTQMNQAFRNIVNMLHGVRD | Rv1038c, Rv3620c |
| | Pep#20 | 3 | RNIVNMLHGVRDGLVRDANN | Rv1038c, Rv1197, Rv1792, Rv2347c, Rv3620c |
| | Pep#25 | 4 | MAQMNQAFRNIVNMLHGVRD | Rv1197, Rv2347c |
| | Pep#29 | 5 | EAEHQAIIRDVLTASDFWGG | Rv1198 |
| | Pep#33 | 6 | LGRNFQVIYEQANAHGQKVQ | Rv1198, Rv2346c, Rv3619c, Rv1037c, Rv1793 |
| | Pep#42 | 7 | RDVLAAGDFWGGAGSVACQE | Rv2346c, Rv1793 |
| | Pep#55 | 8 | QANLGEAAGTYVAADAAAAS | Rv3020c |
| | Pep#57 | 9 | DVDAHGAMIRAQAGSLEAEH | Rv3619c, Rv1037c |
| | Pep#64 | 10 | SAELPDWLAANRGLAPGGHA | Rv3803c |
| Sec#2 | As above but omitting Pep#64 | | | |

Figure 3A:
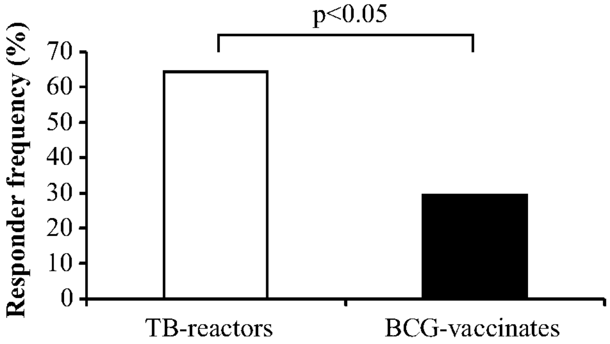
FIG. 3A shows the responder frequency of 22 TB-reactor and 21 BCG-vaccinated animals to the Sec#1 peptide pool ($p<0.05$, Fisher's Exact Test)
Figure 3B:
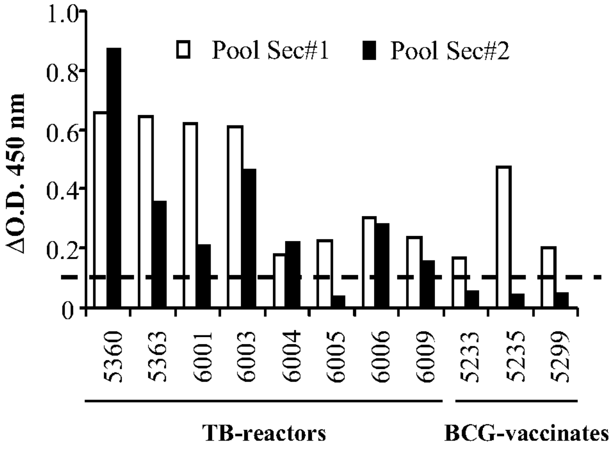
FIG. 3B shows IFN-γ responses ($\Delta OD_{450}$) from 8 TB-reactor and 3 BCG-vaccinated animals to both the Sec#1 and Sec#2 peptide pools, with the dashed horizontal line representing the cut off for a positive response.

As shown in FIG. 3A, the responder frequency to the Sec#1 peptide pool was significantly greater in TB-reactor animals ($p<0.05$, Fisher's Exact Test), with 14 out of 22 (64%) TB-reactor animals recognising the peptide pool compared with 6 out of 21 (29%) BCG-vaccinated animals. In order to optimise the peptide pool for use as a DIVA reagent, the individual peptide components of the Sec#1 peptide pool were re-screened for their ability to induce an IFN-γ response in BCG-vaccinated animals. These experiments identified only a single peptide (peptide #64) as being immunogenic in some BCG-vaccinated animals (data not shown). Thus, a second peptide pool (Sec#2) was constructed that lacked this peptide and the ability of both Sec#1 and Sec#2 to induce IFN-γ was compared in both TB-reactor animals (n=8) and BCG-vaccinated animals (n=3) which had previously demonstrated to recognise the former peptide pool. Omitting peptide #64 from the pool had little effect on the responder frequency for TB-reactor animals, with 7 of the 8 animals still producing IFN-γ □ above the cut off (FIG. 3B). Overall, 7 out of 13 (54%) TB-reactor animals produced IFN-γ in response to Sec#2 (data not shown). In contrast, removal of peptide #64 completely abrogated the response in all BCG-vaccinated animals tested (FIG. 3B).

Figure 4:
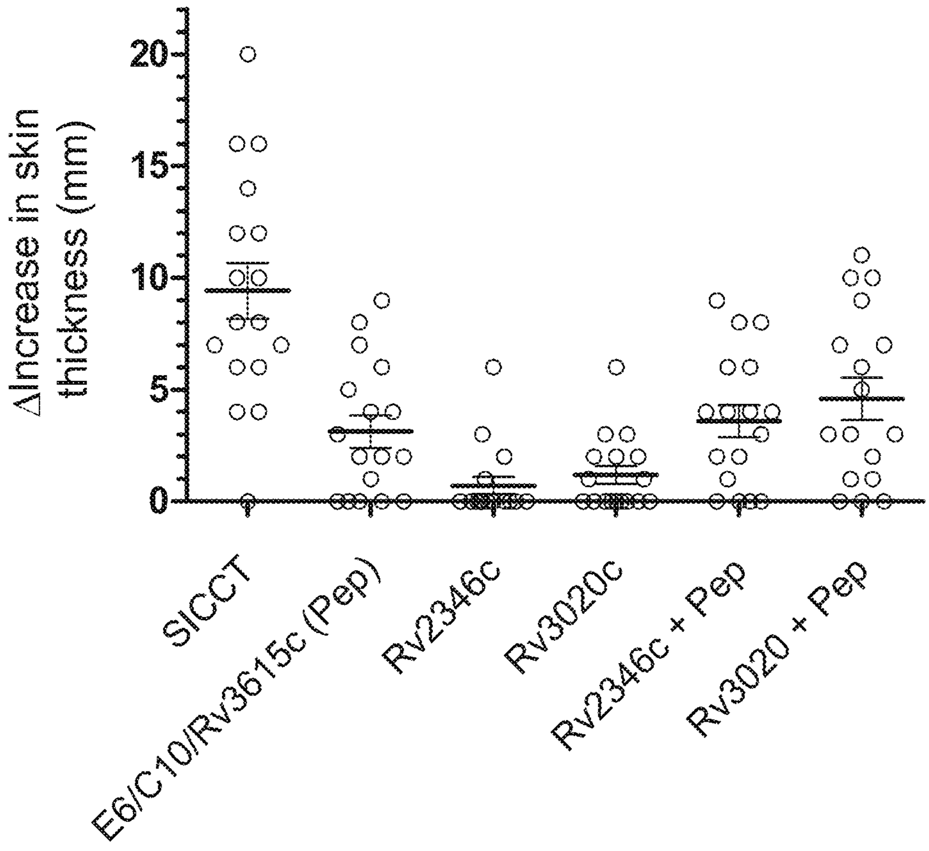
FIG. 4 shows skin-test responses to peptide cocktails in cattle naturally exposed to *M. bovis* infection.
Figure 5:
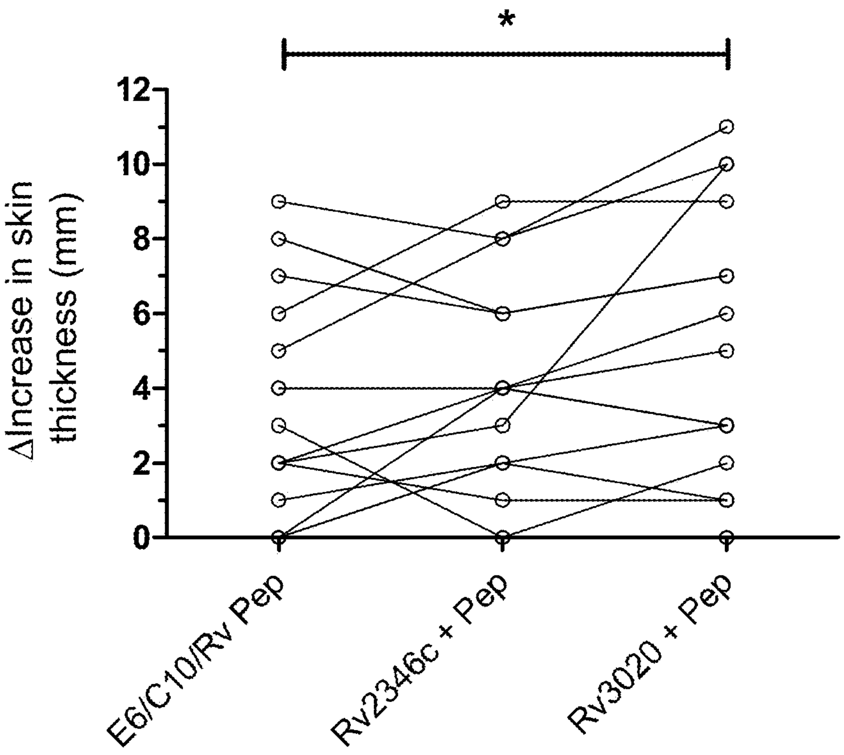
FIG. 5 shows skin-test responses of a reference peptide cocktail containing peptides of ESAT6, CFP10 and Rv3615c either alone or in combination with a peptide cocktail of either Rv2346c (peptide pool #11) or Rv3020c (peptide pool

The skin-test data is shown in FIG. 4. One animal failed to induce a skin-reaction in the comparative tuberculin skin-test and, similarly, this same animal provided no skin-test response to any of the defined antigen combinations. Addition of the peptide cocktail of Rv3020c (SEQ ID NOs:8 and 60-69) to the reference cocktail containing peptides of ESAT-6, CFP-10 and Rv3615c (SEQ ID NOs: 11-43) demonstrated significantly stronger responses than the reference cocktail alone, see FIG. 5.

Discussion

The results presented herein have significant importance with regards to the development of DIVA reagents. Screening of 119 proteins secreted, or potentially secreted, by *M. bovis* revealed three unique peptide pools that were frequently recognized by *M. bovis*-infected cattle but failed to induce an IFN-γ response in any BCG-vaccinated animals studied. Two of these peptide pools consisted of overlapping peptides that represented the full amino acid sequence for two individual antigens, Rv2346c and Rv3020c, whilst the third (Sec#2) consisted of a cocktail of 9 peptides derived from multiple antigens.

The underlying mechanism for the differential recognition of Rv2346c and Rv3020c remains unclear. Firstly, both genes are located in the genomes of *M. bovis* (strain AF2122/97) and, more importantly, in BCG Pasteur (strain 1173P2) which was used to immunise the cattle. Secondly, genome analysis revealed identical amino acid sequences of the two proteins between the two strains. Thus, the lack of immune responses to Rv2346c and Rv3020c seen in BCG-vaccinated animals is unlikely to be explained by deletions or amino acid sequence alterations within these two proteins in the BCG Pasteur strain used for vaccination.

It is unlikely that IFN-γ responses to a single protein antigen will be sufficient for the detection of *M. bovis* infection of cattle. Indeed, the interferon-γ release assay (IGRA) test for human *M. tuberculosis* infection utilizes synthetic peptides from two different *M. tuberculosis* antigens (ESAT-6 and CFP-10). With this in mind, the inventors developed a cocktail (Sec#2) containing individual peptides isolated from various peptide pools representing the most frequently recognised antigens. Interestingly, these antigens were found to belong to the ESAT-6 protein family, highlighting the immunodominance of these antigens. The Sec#2 cocktail contained several immunodominant peptides with restricted expression amongst the ESAT-6 proteins; for example, peptide #55 is located only within Rv3020c while peptide #42 is located in Rv2346c and Rv1793 (Table 3). However, given the high degree of amino acid similarity between the members of the ESAT-6 protein family, several of these peptide sequences represented multiple antigens. For example, peptides #16 and #20 are located in Rv1038c, Rv1197, Rv1792, Rv2347c and Rv3620c, while peptide #33 is located in Rv1198, Rv2346c, Rv3619c, Rv1037c and Rv1793. Thus, without wishing to be bound by theory, targeting these shared sequences not only reduces the number of different components within the DIVA reagent but may also exploit a potential greater antigenic load for these regions.

The ESAT-6/CFP-10 peptide cocktail used in the studies presented herein has been developed as a DIVA reagent in cattle, with reported sensitivities of approximately 78% in *M. bovis*-infected animals (Sidders et al. (2008) Infect. Immun. vo. 76 pp 3932-3939; Vordermeier et al. (2001) Clin. Diagn. Lab. Immunol. vol. 8 pp 571-578). Thus, one area of research of high importance is the identification of reagents that may complement the ESAT-6/CFP-10 peptide cocktail in the diagnosis of bovine TB. Recently, the inventors have demonstrated that 4 out of 7 (57%) *M. bovis*-infected animals that failed to recognise the ESAT-6/CFP-10 peptide cocktail did mount an IFN-γ response to the antigen Rv3615c, theoretically increasing diagnostic sensitivity to 91% without compromising specificity in BCG-vaccinated animals (Sidders et al. (2008) Infect. Immun. vo. 76 pp 3932-3939). In the current study, 5 out of 13 (38%) TB-reactor animals recognized Rv3615c (data not shown), results similar to those previously reported (Sidders et al. (2008)). All of these 5 animals recognized the Sec#2 peptide cocktail, which also induced responses in a further two animals (overall responder frequency of 54%), suggesting that the Sec#2 peptide cocktail may be as good, if not better, at complementing ESAT-6/CFP-10 in the diagnosis of bovine TB without compromising specificity in BCG-vaccinated animals.

Finally, skin test data showed that the peptides improved the sensitivity of skin test detection of *M. bovis* infected cattle when using a cocktail of ESAT-6, CFP-10 and Rv3615c peptides.

In summary, the results of this study demonstrate that cocktails of synthetic peptides derived from secreted or potentially secreted antigens have the capacity to distinguish between *M. bovis*-infected and BCG-vaccinated animals in blood-based screening assays.

The invention claimed is:

1. A diagnostic reagent comprising a polypeptide consisting of amino acid sequence QANLGEAAGTYVAADAAAAS (SEQ ID NO:8), wherein the diagnostic reagent is a sterile injectable preparation, and the diagnostic reagent optionally further comprises a polypeptide consisting of amino acid sequence MTENLTVQPERLGVLASHHDNAAVDASSGVEAAAGLGESVAITHGPYCSQFNDTLNVYLTAHNALGSSLHTAGVDLAKSLRIAAKIY SEADEAWRKAIDGLFT (SEQ ID NO:46).

2. A method of detecting a tuberculosis infection in an animal, or exposure of an animal to a tuberculosis agent, comprising the steps of (i) contacting a population of cells from the animal with at least one diagnostic reagent as defined in claim 1; and (ii) determining whether the cells of said population recognise the diagnostic reagent;

optionally wherein the population of cells includes T-cells.

3. The method of claim 2, comprising a cell-mediated immunity (CMI) assay, optionally wherein the CMI assay detects interferon gamma (IFN-γ).

4. A method of detecting a tuberculosis infection in an animal, or exposure of an animal to a tuberculosis agent, comprising conducting a skin test on the animal using at least one diagnostic reagent as defined in claim 1.

5. A diagnostic kit comprising at least one diagnostic reagent as defined in claim 1.

6. The kit of claim 5 in which the diagnostic reagent is able to detect a tuberculosis infection in an animal, or exposure of an animal to a tuberculosis agent.

7. The diagnostic reagent of claim 1, wherein the sterile injectable preparation is an aqueous or an oleaginous suspension, or a suspension in a non-toxic parenterally-acceptable diluent or solvent.

8. The diagnostic reagent of claim 1, which is suitable for use to differentiate between an animal having a tuberculosis infection and an animal vaccinated against tuberculosis infection.

9. A diagnostic reagent comprising a polypeptide consisting of amino acid sequence QANLGEAAGTYVAADAAAAS (SEQ ID NO:8), the diagnostic reagent optionally further comprising a polypeptide consisting of amino acid sequence MTENLTVQPERLGVLASHHDNAAVDASSGVEAAAGLGESVAITHGPYCSQFNDTLNVYLTAHNALGSSLHTAGVDLAKSLRIAAKIYSEADEAWRKAIDGLFT (SEQ ID NO:46), wherein the diagnostic reagent is a sterile injectable preparation, and wherein the diagnostic reagent is capable of eliciting a positive result when used in an assay to determine whether an animal has a tuberculosis infection or has been exposed to a tuberculosis agent, is capable of eliciting a negative result when the animal has been vaccinated against infection by a tuberculosis agent, and is capable of eliciting a negative result when the animal is unvaccinated and uninfected or unexposed to a tuberculosis agent.

10. The diagnostic reagent of claim 9, wherein the sterile injectable preparation is an aqueous or an oleaginous suspension, or a suspension in a non-toxic parenterally-acceptable diluent or solvent.

* * * * *

SEQUENCE LISTING

```
<160> NUMBER OF SEQ ID NOS: 70

<210> SEQ ID NO 1
<211> LENGTH: 20
<212> TYPE: PRT
<213> ORGANISM: Mycobacterium bovis

<400> SEQUENCE: 1

Met Trp Ala Ser Ala Gln Asn Ile Ser Gly Ala Gly Trp Ser Gly Met
1               5                   10                  15

Ala Glu Ala Thr
            20


<210> SEQ ID NO 2
<211> LENGTH: 20
<212> TYPE: PRT
<213> ORGANISM: Mycobacterium bovis

<400> SEQUENCE: 2

Met Thr Gln Met Asn Gln Ala Phe Arg Asn Ile Val Asn Met Leu His
1               5                   10                  15

Gly Val Arg Asp
            20


<210> SEQ ID NO 3
<211> LENGTH: 20
<212> TYPE: PRT
<213> ORGANISM: Mycobacterium bovis

<400> SEQUENCE: 3

Arg Asn Ile Val Asn Met Leu His Gly Val Arg Asp Gly Leu Val Arg
1               5                   10                  15

Asp Ala Asn Asn
            20


<210> SEQ ID NO 4
<211> LENGTH: 20
<212> TYPE: PRT
<213> ORGANISM: Mycobacterium bovis

<400> SEQUENCE: 4

Met Ala Gln Met Asn Gln Ala Phe Arg Asn Ile Val Asn Met Leu His
1               5                   10                  15

Gly Val Arg Asp
            20


<210> SEQ ID NO 5
<211> LENGTH: 20
<212> TYPE: PRT
<213> ORGANISM: Mycobacterium bovis
```

<400> SEQUENCE: 5

```
Glu Ala Glu His Gln Ala Ile Ile Arg Asp Val Leu Thr Ala Ser Asp
1               5                   10                  15

Phe Trp Gly Gly
            20
```

<210> SEQ ID NO 6
<211> LENGTH: 20
<212> TYPE: PRT
<213> ORGANISM: Mycobacterium bovis

<400> SEQUENCE: 6

```
Leu Gly Arg Asn Phe Gln Val Ile Tyr Glu Gln Ala Asn Ala His Gly
1               5                   10                  15

Gln Lys Val Gln
            20
```

<210> SEQ ID NO 7
<211> LENGTH: 20
<212> TYPE: PRT
<213> ORGANISM: Mycobacterium bovis

<400> SEQUENCE: 7

```
Arg Asp Val Leu Ala Ala Gly Asp Phe Trp Gly Gly Ala Gly Ser Val
1               5                   10                  15

Ala Cys Gln Glu
            20
```

<210> SEQ ID NO 8
<211> LENGTH: 20
<212> TYPE: PRT
<213> ORGANISM: Mycobacterium bovis

<400> SEQUENCE: 8

```
Gln Ala Asn Leu Gly Glu Ala Ala Gly Thr Tyr Val Ala Ala Asp Ala
1               5                   10                  15

Ala Ala Ala Ser
            20
```

<210> SEQ ID NO 9
<211> LENGTH: 20
<212> TYPE: PRT
<213> ORGANISM: Mycobacterium bovis

<400> SEQUENCE: 9

```
Asp Val Asp Ala His Gly Ala Met Ile Arg Ala Gln Ala Gly Ser Leu
1               5                   10                  15

Glu Ala Glu His
            20
```

<210> SEQ ID NO 10
<211> LENGTH: 20
<212> TYPE: PRT
<213> ORGANISM: Mycobacterium bovis

<400> SEQUENCE: 10

```
Ser Ala Glu Leu Pro Asp Trp Leu Ala Ala Asn Arg Gly Leu Ala Pro
1               5                   10                  15

Gly Gly His Ala
            20
```

<210> SEQ ID NO 11
<211> LENGTH: 16
<212> TYPE: PRT
<213> ORGANISM: Mycobacterium bovis

<400> SEQUENCE: 11

Met Thr Glu Gln Gln Trp Asn Phe Ala Gly Ile Glu Ala Ala Ala Ser
1 5 10 15

<210> SEQ ID NO 12
<211> LENGTH: 16
<212> TYPE: PRT
<213> ORGANISM: Mycobacterium bovis

<400> SEQUENCE: 12

Ala Gly Ile Glu Ala Ala Ala Ser Ala Ile Gln Gly Asn Val Thr Ser
1 5 10 15

<210> SEQ ID NO 13
<211> LENGTH: 16
<212> TYPE: PRT
<213> ORGANISM: Mycobacterium bovis

<400> SEQUENCE: 13

Ala Ile Gln Gly Asn Val Thr Ser Ile His Ser Leu Leu Asp Glu Gly
1 5 10 15

<210> SEQ ID NO 14
<211> LENGTH: 16
<212> TYPE: PRT
<213> ORGANISM: Mycobacterium bovis

<400> SEQUENCE: 14

Ile His Ser Leu Leu Asp Glu Gly Lys Gln Ser Leu Thr Lys Leu Ala
1 5 10 15

<210> SEQ ID NO 15
<211> LENGTH: 16
<212> TYPE: PRT
<213> ORGANISM: Mycobacterium bovis

<400> SEQUENCE: 15

Lys Gln Ser Leu Thr Lys Leu Ala Ala Ala Trp Gly Gly Ser Gly Ser
1 5 10 15

<210> SEQ ID NO 16
<211> LENGTH: 16
<212> TYPE: PRT
<213> ORGANISM: Mycobacterium bovis

<400> SEQUENCE: 16

Ala Ala Trp Gly Gly Ser Gly Ser Glu Ala Tyr Gln Gly Val Gln Gln
1 5 10 15

<210> SEQ ID NO 17
<211> LENGTH: 16
<212> TYPE: PRT
<213> ORGANISM: Mycobacterium bovis

<400> SEQUENCE: 17

Glu Ala Tyr Gln Gly Val Gln Gln Lys Trp Asp Ala Thr Ala Thr Glu
1 5 10 15

<210> SEQ ID NO 18

-continued

<211> LENGTH: 16
<212> TYPE: PRT
<213> ORGANISM: Mycobacterium bovis

<400> SEQUENCE: 18

Lys Trp Asp Ala Thr Ala Thr Glu Leu Asn Asn Ala Leu Gln Asn Leu
1 5 10 15

<210> SEQ ID NO 19
<211> LENGTH: 16
<212> TYPE: PRT
<213> ORGANISM: Mycobacterium bovis

<400> SEQUENCE: 19

Leu Asn Asn Ala Leu Gln Asn Leu Ala Arg Thr Ile Ser Glu Ala Gly
1 5 10 15

<210> SEQ ID NO 20
<211> LENGTH: 16
<212> TYPE: PRT
<213> ORGANISM: Mycobacterium bovis

<400> SEQUENCE: 20

Ala Arg Thr Ile Ser Glu Ala Gly Gln Ala Met Ala Ser Thr Glu Gly
1 5 10 15

<210> SEQ ID NO 21
<211> LENGTH: 15
<212> TYPE: PRT
<213> ORGANISM: Mycobacterium bovis

<400> SEQUENCE: 21

Gln Ala Met Ala Ser Thr Glu Gly Asn Val Thr Gly Met Phe Ala
1 5 10 15

<210> SEQ ID NO 22
<211> LENGTH: 18
<212> TYPE: PRT
<213> ORGANISM: Mycobacterium bovis

<400> SEQUENCE: 22

Met Ala Glu Met Lys Thr Asp Ala Ala Thr Leu Ala Gln Glu Ala Gly
1 5 10 15

Asn Phe

<210> SEQ ID NO 23
<211> LENGTH: 16
<212> TYPE: PRT
<213> ORGANISM: Mycobacterium bovis

<400> SEQUENCE: 23

Gln Glu Ala Gly Asn Phe Glu Arg Ile Ser Gly Asp Leu Lys Thr Gln
1 5 10 15

<210> SEQ ID NO 24
<211> LENGTH: 18
<212> TYPE: PRT
<213> ORGANISM: Mycobacterium bovis

<400> SEQUENCE: 24

Glu Arg Ile Ser Gly Asp Leu Lys Thr Gln Ile Asp Gln Val Glu Ser
1 5 10 15

Thr Ala

<210> SEQ ID NO 25
<211> LENGTH: 17
<212> TYPE: PRT
<213> ORGANISM: Mycobacterium bovis

<400> SEQUENCE: 25

Ile Asp Gln Val Glu Ser Thr Ala Gly Ser Leu Gln Gly Gln Trp Arg
1               5                   10                  15

Gly

<210> SEQ ID NO 26
<211> LENGTH: 18
<212> TYPE: PRT
<213> ORGANISM: Mycobacterium bovis

<400> SEQUENCE: 26

Gly Ser Leu Gln Gly Gln Trp Arg Gly Ala Ala Gly Thr Ala Ala Gln
1               5                   10                  15

Ala Ala

<210> SEQ ID NO 27
<211> LENGTH: 18
<212> TYPE: PRT
<213> ORGANISM: Mycobacterium bovis

<400> SEQUENCE: 27

Ala Gly Thr Ala Ala Gln Ala Ala Val Val Arg Phe Gln Glu Ala Ala
1               5                   10                  15

Asn Lys

<210> SEQ ID NO 28
<211> LENGTH: 18
<212> TYPE: PRT
<213> ORGANISM: Mycobacterium bovis

<400> SEQUENCE: 28

Val Val Arg Phe Gln Glu Ala Ala Asn Lys Gln Lys Gln Glu Leu Asp
1               5                   10                  15

Glu Ile

<210> SEQ ID NO 29
<211> LENGTH: 20
<212> TYPE: PRT
<213> ORGANISM: Mycobacterium bovis

<400> SEQUENCE: 29

Gln Lys Gln Glu Leu Asp Glu Ile Ser Thr Asn Ile Arg Gln Ala Gly
1               5                   10                  15

Val Gln Tyr Ser
            20

<210> SEQ ID NO 30
<211> LENGTH: 18
<212> TYPE: PRT
<213> ORGANISM: Mycobacterium bovis

<400> SEQUENCE: 30

Asn Ile Arg Gln Ala Gly Val Gln Tyr Ser Arg Ala Asp Glu Glu Gln
1               5                   10                  15

Gln Gln

<210> SEQ ID NO 31
<211> LENGTH: 16
<212> TYPE: PRT
<213> ORGANISM: Mycobacterium bovis

<400> SEQUENCE: 31

Arg Ala Asp Glu Glu Gln Gln Gln Ala Leu Ser Ser Gln Met Gly Phe
1 5 10 15

<210> SEQ ID NO 32
<211> LENGTH: 20
<212> TYPE: PRT
<213> ORGANISM: Mycobacterium bovis

<400> SEQUENCE: 32

Met Thr Glu Asn Leu Thr Val Gln Pro Glu Arg Leu Gly Val Leu Ala
1 5 10 15

Ser His His Asp
20

<210> SEQ ID NO 33
<211> LENGTH: 20
<212> TYPE: PRT
<213> ORGANISM: Mycobacterium bovis

<400> SEQUENCE: 33

Pro Glu Arg Leu Gly Val Leu Ala Ser His His Asp Asn Ala Ala Val
1 5 10 15

Asp Ala Ser Ser
20

<210> SEQ ID NO 34
<211> LENGTH: 20
<212> TYPE: PRT
<213> ORGANISM: Mycobacterium bovis

<400> SEQUENCE: 34

Ser His His Asp Asn Ala Ala Val Asp Ala Ser Ser Gly Val Glu Ala
1 5 10 15

Ala Ala Gly Leu
20

<210> SEQ ID NO 35
<211> LENGTH: 20
<212> TYPE: PRT
<213> ORGANISM: Mycobacterium bovis

<400> SEQUENCE: 35

Asp Ala Ser Ser Gly Val Glu Ala Ala Ala Gly Leu Gly Glu Ser Val
1 5 10 15

Ala Ile Thr His
20

<210> SEQ ID NO 36
<211> LENGTH: 20
<212> TYPE: PRT
<213> ORGANISM: Mycobacterium bovis

<400> SEQUENCE: 36

Ala Ala Gly Leu Gly Glu Ser Val Ala Ile Thr His Gly Pro Tyr Cys
1 5 10 15

Ser Gln Phe Asn

20

<210> SEQ ID NO 37
<211> LENGTH: 20
<212> TYPE: PRT
<213> ORGANISM: Mycobacterium bovis

<400> SEQUENCE: 37

Ala Ile Thr His Gly Pro Tyr Cys Ser Gln Phe Asn Asp Thr Leu Asn
1 5 10 15

Val Tyr Leu Thr
20

<210> SEQ ID NO 38
<211> LENGTH: 20
<212> TYPE: PRT
<213> ORGANISM: Mycobacterium bovis

<400> SEQUENCE: 38

Ser Gln Phe Asn Asp Thr Leu Asn Val Tyr Leu Thr Ala His Asn Ala
1 5 10 15

Leu Gly Ser Ser
20

<210> SEQ ID NO 39
<211> LENGTH: 20
<212> TYPE: PRT
<213> ORGANISM: Mycobacterium bovis

<400> SEQUENCE: 39

Val Tyr Leu Thr Ala His Asn Ala Leu Gly Ser Ser Leu His Thr Ala
1 5 10 15

Gly Val Asp Leu
20

<210> SEQ ID NO 40
<211> LENGTH: 20
<212> TYPE: PRT
<213> ORGANISM: Mycobacterium bovis

<400> SEQUENCE: 40

Leu Gly Ser Ser Leu His Thr Ala Gly Val Asp Leu Ala Lys Ser Leu
1 5 10 15

Arg Ile Ala Ala
20

<210> SEQ ID NO 41
<211> LENGTH: 20
<212> TYPE: PRT
<213> ORGANISM: Mycobacterium bovis

<400> SEQUENCE: 41

Gly Val Asp Leu Ala Lys Ser Leu Arg Ile Ala Ala Lys Ile Tyr Ser
1 5 10 15

Glu Ala Asp Glu
20

<210> SEQ ID NO 42
<211> LENGTH: 20
<212> TYPE: PRT
<213> ORGANISM: Mycobacterium bovis

<400> SEQUENCE: 42

-continued

Arg Ile Ala Ala Lys Ile Tyr Ser Glu Ala Asp Glu Ala Trp Arg Lys
1 5 10 15

Ala Ile Asp Gly
20

<210> SEQ ID NO 43
<211> LENGTH: 20
<212> TYPE: PRT
<213> ORGANISM: Mycobacterium bovis

<400> SEQUENCE: 43

Ala Lys Ile Tyr Ser Glu Ala Asp Glu Ala Trp Arg Lys Ala Ile Asp
1 5 10 15

Gly Leu Phe Tyr
20

<210> SEQ ID NO 44
<211> LENGTH: 95
<212> TYPE: PRT
<213> ORGANISM: Mycobacterium bovis

<400> SEQUENCE: 44

Met Thr Glu Gln Gln Trp Asn Phe Ala Gly Ile Glu Ala Ala Ala Ser
1 5 10 15

Ala Ile Gln Gly Asn Val Thr Ser Ile His Ser Leu Leu Asp Glu Gly
20 25 30

Lys Gln Ser Leu Thr Lys Leu Ala Ala Ala Trp Gly Gly Ser Gly Ser
35 40 45

Glu Ala Tyr Gln Gly Val Gln Gln Lys Trp Asp Ala Thr Ala Thr Glu
50 55 60

Leu Asn Asn Ala Leu Gln Asn Leu Ala Arg Thr Ile Ser Glu Ala Gly
65 70 75 80

Gln Ala Met Ala Ser Thr Glu Gly Asn Val Thr Gly Met Phe Ala
85 90 95

<210> SEQ ID NO 45
<211> LENGTH: 100
<212> TYPE: PRT
<213> ORGANISM: Mycobacterium bovis

<400> SEQUENCE: 45

Met Ala Glu Met Lys Thr Asp Ala Ala Thr Leu Ala Gln Glu Ala Gly
1 5 10 15

Asn Phe Glu Arg Ile Ser Gly Asp Leu Lys Thr Gln Ile Asp Gln Val
20 25 30

Glu Ser Thr Ala Gly Ser Leu Gln Gly Gln Trp Arg Gly Ala Ala Gly
35 40 45

Thr Ala Ala Gln Ala Ala Val Val Arg Phe Gln Glu Ala Ala Asn Lys
50 55 60

Gln Lys Gln Glu Leu Asp Glu Ile Ser Thr Asn Ile Arg Gln Ala Gly
65 70 75 80

Val Gln Tyr Ser Arg Ala Asp Glu Glu Gln Gln Gln Ala Leu Ser Ser
85 90 95

Gln Met Gly Phe
100

<210> SEQ ID NO 46
<211> LENGTH: 103

<212> TYPE: PRT
<213> ORGANISM: Mycobacterium bovis

<400> SEQUENCE: 46

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100

<210> SEQ ID NO 47
<211> LENGTH: 220
<212> TYPE: PRT
<213> ORGANISM: Mycobacterium bovis

<400> SEQUENCE: 47

Met Ile Asn Val Gln Ala Lys Pro Ala Ala Ala Ala Ser Leu Ala Ala
1               5                   10                  15

Ile Ala Ile Ala Phe Leu Ala Gly Cys Ser Ser Thr Lys Pro Val Ser
            20                  25                  30

Gln Asp Thr Ser Pro Lys Pro Ala Thr Ser Pro Ala Ala Pro Val Thr
        35                  40                  45

Thr Ala Ala Met Ala Asp Pro Ala Ala Asp Leu Ile Gly Arg Gly Cys
    50                  55                  60

Ala Gln Tyr Ala Ala Gln Asn Pro Thr Gly Pro Gly Ser Val Ala Gly
65                  70                  75                  80

Met Ala Gln Asp Pro Val Ala Thr Ala Ala Ser Asn Asn Pro Met Leu
                85                  90                  95

Ser Thr Leu Thr Ser Ala Leu Ser Gly Lys Leu Asn Pro Asp Val Asn
            100                 105                 110

Leu Val Asp Thr Leu Asn Gly Gly Glu Tyr Thr Val Phe Ala Pro Thr
        115                 120                 125

Asn Ala Ala Phe Asp Lys Leu Pro Ala Ala Thr Ile Asp Gln Leu Lys
    130                 135                 140

Thr Asp Ala Lys Leu Leu Ser Ser Ile Leu Thr Tyr His Val Ile Ala
145                 150                 155                 160

Gly Gln Ala Ser Pro Ser Arg Ile Asp Gly Thr His Gln Thr Leu Gln
                165                 170                 175

Gly Ala Asp Leu Thr Val Ile Gly Ala Arg Asp Asp Leu Met Val Asn
            180                 185                 190

Asn Ala Gly Leu Val Cys Gly Gly Val His Thr Ala Asn Ala Thr Val
        195                 200                 205

Tyr Met Ile Asp Thr Val Leu Met Pro Pro Ala Gln
    210                 215                 220

<210> SEQ ID NO 48
<211> LENGTH: 20

```
<212> TYPE: PRT
<213> ORGANISM: Mycobacterium bovis

<400> SEQUENCE: 48

Gly Leu Val Cys Gly Gly Val His Thr Ala Asn Ala Thr Val Tyr Met
1               5                   10                  15

Ile Asp Thr Val
            20


<210> SEQ ID NO 49
<211> LENGTH: 193
<212> TYPE: PRT
<213> ORGANISM: Mycobacterium bovis

<400> SEQUENCE: 49

Met Lys Val Lys Asn Thr Ile Ala Ala Thr Ser Phe Ala Ala Ala Gly
1               5                   10                  15

Leu Ala Ala Leu Ala Val Ala Val Ser Pro Pro Ala Ala Ala Gly Asp
            20                  25                  30

Leu Val Gly Pro Gly Cys Ala Glu Tyr Ala Ala Ala Asn Pro Thr Gly
        35                  40                  45

Pro Ala Ser Val Gln Gly Met Ser Gln Asp Pro Val Ala Val Ala Ala
    50                  55                  60

Ser Asn Asn Pro Glu Leu Thr Thr Leu Thr Ala Ala Leu Ser Gly Gln
65                  70                  75                  80

Leu Asn Pro Gln Val Asn Leu Val Asp Thr Leu Asn Ser Gly Gln Tyr
                85                  90                  95

Thr Val Phe Ala Pro Thr Asn Ala Ala Phe Ser Lys Leu Pro Ala Ser
            100                 105                 110

Thr Ile Asp Glu Leu Lys Thr Asn Ser Ser Leu Leu Thr Ser Ile Leu
        115                 120                 125

Thr Tyr His Val Val Ala Gly Gln Thr Ser Pro Ala Asn Val Val Gly
    130                 135                 140

Thr Arg Gln Thr Leu Gln Gly Ala Ser Val Thr Val Thr Gly Gln Gly
145                 150                 155                 160

Asn Ser Leu Lys Val Gly Asn Ala Asp Val Val Cys Gly Gly Val Ser
                165                 170                 175

Thr Ala Asn Ala Thr Val Tyr Met Ile Asp Ser Val Leu Met Pro Pro
            180                 185                 190

Ala


<210> SEQ ID NO 50
<211> LENGTH: 20
<212> TYPE: PRT
<213> ORGANISM: Mycobacterium bovis

<400> SEQUENCE: 50

Met Thr Ile Asn Tyr Gln Phe Gly Asp Val Asp Ala His Gly Ala Met
1               5                   10                  15

Ile Arg Ala Gln
            20


<210> SEQ ID NO 51
<211> LENGTH: 20
<212> TYPE: PRT
<213> ORGANISM: Mycobacterium bovis

<400> SEQUENCE: 51
```

-continued

Asp Val Asp Ala His Gly Ala Met Ile Arg Ala Gln Ala Gly Leu Leu
1 5 10 15

Glu Ala Glu His
20

<210> SEQ ID NO 52
<211> LENGTH: 20
<212> TYPE: PRT
<213> ORGANISM: Mycobacterium bovis

<400> SEQUENCE: 52

Ile Arg Ala Gln Ala Gly Leu Leu Glu Ala Glu His Gln Ala Ile Val
1 5 10 15

Arg Asp Val Leu
20

<210> SEQ ID NO 53
<211> LENGTH: 20
<212> TYPE: PRT
<213> ORGANISM: Mycobacterium bovis

<400> SEQUENCE: 53

Glu Ala Glu His Gln Ala Ile Val Arg Asp Val Leu Ala Ala Gly Asp
1 5 10 15

Phe Trp Gly Gly
20

<210> SEQ ID NO 54
<211> LENGTH: 20
<212> TYPE: PRT
<213> ORGANISM: Mycobacterium bovis

<400> SEQUENCE: 54

Phe Trp Gly Gly Ala Gly Ser Val Ala Cys Gln Glu Phe Ile Thr Gln
1 5 10 15

Leu Gly Arg Asn
20

<210> SEQ ID NO 55
<211> LENGTH: 20
<212> TYPE: PRT
<213> ORGANISM: Mycobacterium bovis

<400> SEQUENCE: 55

Ala Cys Gln Glu Phe Ile Thr Gln Leu Gly Arg Asn Phe Gln Val Ile
1 5 10 15

Tyr Glu Gln Ala
20

<210> SEQ ID NO 56
<211> LENGTH: 20
<212> TYPE: PRT
<213> ORGANISM: Mycobacterium bovis

<400> SEQUENCE: 56

Leu Gly Arg Asn Phe Gln Val Ile Tyr Glu Gln Ala Asn Ala His Gly
1 5 10 15

Gln Lys Val Gln
20

<210> SEQ ID NO 57
<211> LENGTH: 20

-continued

<212> TYPE: PRT
<213> ORGANISM: Mycobacterium bovis

<400> SEQUENCE: 57

Tyr Glu Gln Ala Asn Ala His Gly Gln Lys Val Gln Ala Ala Gly Asn
1 5 10 15

Asn Met Ala Gln
20

<210> SEQ ID NO 58
<211> LENGTH: 20
<212> TYPE: PRT
<213> ORGANISM: Mycobacterium bovis

<400> SEQUENCE: 58

Gln Lys Val Gln Ala Ala Gly Asn Asn Met Ala Gln Thr Asp Ser Ala
1 5 10 15

Val Gly Ser Ser
20

<210> SEQ ID NO 59
<211> LENGTH: 20
<212> TYPE: PRT
<213> ORGANISM: Mycobacterium bovis

<400> SEQUENCE: 59

Val Gln Ala Ala Gly Asn Asn Met Ala Gln Thr Asp Ser Ala Val Gly
1 5 10 15

Ser Ser Trp Ala
20

<210> SEQ ID NO 60
<211> LENGTH: 20
<212> TYPE: PRT
<213> ORGANISM: Mycobacterium bovis

<400> SEQUENCE: 60

Met Ser Leu Leu Asp Ala His Ile Pro Gln Leu Ile Ala Ser His Thr
1 5 10 15

Ala Phe Ala Ala
20

<210> SEQ ID NO 61
<211> LENGTH: 20
<212> TYPE: PRT
<213> ORGANISM: Mycobacterium bovis

<400> SEQUENCE: 61

Pro Gln Leu Ile Ala Ser His Thr Ala Phe Ala Ala Lys Ala Gly Leu
1 5 10 15

Met Arg His Thr
20

<210> SEQ ID NO 62
<211> LENGTH: 20
<212> TYPE: PRT
<213> ORGANISM: Mycobacterium bovis

<400> SEQUENCE: 62

Ala Phe Ala Ala Lys Ala Gly Leu Met Arg His Thr Ile Gly Gln Ala
1 5 10 15

Glu Gln Gln Ala

-continued

20

<210> SEQ ID NO 63
<211> LENGTH: 20
<212> TYPE: PRT
<213> ORGANISM: Mycobacterium bovis

<400> SEQUENCE: 63

Met Arg His Thr Ile Gly Gln Ala Glu Gln Gln Ala Met Ser Ala Gln
1               5                   10                  15

Ala Phe His Gln
            20

<210> SEQ ID NO 64
<211> LENGTH: 20
<212> TYPE: PRT
<213> ORGANISM: Mycobacterium bovis

<400> SEQUENCE: 64

Glu Gln Gln Ala Met Ser Ala Gln Ala Phe His Gln Gly Glu Ser Ala
1               5                   10                  15

Ala Ala Phe Gln
            20

<210> SEQ ID NO 65
<211> LENGTH: 20
<212> TYPE: PRT
<213> ORGANISM: Mycobacterium bovis

<400> SEQUENCE: 65

Ala Phe His Gln Gly Glu Ser Ala Ala Ala Phe Gln Gly Ala His Ala
1               5                   10                  15

Arg Phe Val Ala
            20

<210> SEQ ID NO 66
<211> LENGTH: 20
<212> TYPE: PRT
<213> ORGANISM: Mycobacterium bovis

<400> SEQUENCE: 66

Ala Ala Phe Gln Gly Ala His Ala Arg Phe Val Ala Ala Ala Ala Lys
1               5                   10                  15

Val Asn Thr Leu
            20

<210> SEQ ID NO 67
<211> LENGTH: 20
<212> TYPE: PRT
<213> ORGANISM: Mycobacterium bovis

<400> SEQUENCE: 67

Arg Phe Val Ala Ala Ala Ala Lys Val Asn Thr Leu Leu Asp Ile Ala
1               5                   10                  15

Gln Ala Asn Leu
            20

<210> SEQ ID NO 68
<211> LENGTH: 20
<212> TYPE: PRT
<213> ORGANISM: Mycobacterium bovis

<400> SEQUENCE: 68

-continued

```
Val Asn Thr Leu Leu Asp Ile Ala Gln Ala Asn Leu Gly Glu Ala Ala
1               5                   10                  15

Gly Thr Tyr Val
            20


<210> SEQ ID NO 69
<211> LENGTH: 20
<212> TYPE: PRT
<213> ORGANISM: Mycobacterium bovis

<400> SEQUENCE: 69

Glu Ala Ala Gly Thr Tyr Val Ala Ala Asp Ala Ala Ala Ala Ser Ser
1               5                   10                  15

Tyr Thr Gly Phe
            20


<210> SEQ ID NO 70
<211> LENGTH: 97
<212> TYPE: PRT
<213> ORGANISM: Mycobacterium bovis

<400> SEQUENCE: 70

Met Ser Leu Leu Asp Ala His Ile Pro Gln Leu Ile Ala Ser His Thr
1               5                   10                  15

Ala Phe Ala Ala Lys Ala Gly Leu Met Arg His Thr Ile Gly Gln Ala
            20                  25                  30

Glu Gln Gln Ala Met Ser Ala Gln Ala Phe His Gln Gly Glu Ser Ala
        35                  40                  45

Ala Ala Phe Gln Gly Ala His Ala Arg Phe Val Ala Ala Ala Ala Lys
    50                  55                  60

Val Asn Thr Leu Leu Asp Ile Ala Gln Ala Asn Leu Gly Glu Ala Ala
65                  70                  75                  80

Gly Thr Tyr Val Ala Ala Asp Ala Ala Ala Ala Ser Ser Tyr Thr Gly
                85                  90                  95

Phe
```